US008337479B2

(12) United States Patent
Nilsson et al.

(10) Patent No.: US 8,337,479 B2
(45) Date of Patent: Dec. 25, 2012

(54) REFASTENABLE PANT-LIKE ABSORBENT ARTICLE AND A METHOD FOR MAKING IT

(75) Inventors: Lennart Nilsson, Skärhamn (SE); Ingemar Fernfors, Mölndal (SE); Christian Järpenberg, Landvetter (SE)

(73) Assignee: SCA Hygiene Products AB, Gothenburg (SE)

( * ) Notice: Subject to any disclaimer, the term of this patent is extended or adjusted under 35 U.S.C. 154(b) by 717 days.

(21) Appl. No.: 12/097,593

(22) PCT Filed: Dec. 19, 2005

(86) PCT No.: PCT/SE2005/001977
§ 371 (c)(1),
(2), (4) Date: Jun. 16, 2008

(87) PCT Pub. No.: WO2007/073247
PCT Pub. Date: Jun. 28, 2007

(65) Prior Publication Data
US 2009/0254059 A1    Oct. 8, 2009

(51) Int. Cl.
*A61F 13/15* (2006.01)
*A61F 13/20* (2006.01)

(52) U.S. Cl. .................... 604/387; 604/396

(58) Field of Classification Search ........... 604/385.01, 604/385.03, 386–387, 389–392, 394, 396
See application file for complete search history.

(56) References Cited

U.S. PATENT DOCUMENTS 5,690,626 A * 11/1997 Suzuki et al. ........ 604/385.25
6,210,388 B1    4/2001  Widlund et al.
6,409,858 B1    6/2002  Popp et al.
7,449,016 B2 * 11/2008  Sugito .................. 604/385.26
2003/0055389 A1  3/2003  Sanders et al.
2003/0125702 A1  7/2003  Couture-Dorschner et al.
2003/0135184 A1  7/2003  Van Gompel et al.
(Continued)

FOREIGN PATENT DOCUMENTS
EP    1 035 818 (B1)    9/2000
(Continued)

OTHER PUBLICATIONS

English language translation of an Official Action dated Dec. 20, 2010, issued by the Japanese Patent Office in corresponding Japanese Patent Application No. 2008-547145.

(Continued)

*Primary Examiner* — Michele M Kidwell
(74) *Attorney, Agent, or Firm* — Buchanan Ingersoll & Rooney PC

(57) ABSTRACT

A pant-type absorbent article including a first body panel having a body facing side and a garment facing side and a second body panel having a body facing side and a garment facing side, the body facing sides of first and second body panels are held together in a face-to-face relationship along lateral edges to form side connections. The article further including a first fastening member hingedly attached to or near a lateral edge of the body facing side of the first body panel and having a portion which is unattached to said first body panel, said portion is refastenably attached to a complementary second fastening member provided on the body facing side of the second body panel. A recess forming a finger grip may be provided in the lateral edge of the first body panel.

21 Claims, 6 Drawing Sheets

U.S. PATENT DOCUMENTS

| | | | |
|---|---|---|---|
| 2003/0135192 A1 | 7/2003 | Guralski et al. | |
| 2005/0043701 A1 | 2/2005 | Otsubo et al. | |
| 2005/0192553 A1 | 9/2005 | Hasler et al. | |
| 2008/0249493 A1* | 10/2008 | Kobayashi et al. | 604/378 |

FOREIGN PATENT DOCUMENTS

| | | | |
|---|---|---|---|
| EP | 1 795 163 | | 6/2007 |
| GB | 2 244 422 A | * | 12/1991 |
| JP | H09-511425 | | 11/1997 |
| JP | 2001-301743 A | | 10/2001 |
| JP | 2002-518095 | | 6/2002 |
| JP | 2004-033348 A | | 2/2004 |
| JP | 2005-095588 A | | 4/2005 |
| JP | 2005-537039 | | 12/2005 |
| JP | 2006-141992 A | | 6/2006 |
| WO | WO 95/27460 | | 10/1995 |
| WO | WO 95/27462 (A1) | | 10/1995 |
| WO | WO 99/65438 | | 12/1999 |
| WO | WO 01/87204 (A1) | | 11/2001 |
| WO | WO 03/024377 (A2) | | 3/2003 |
| WO | WO 03/057116 (A1) | | 7/2003 |
| WO | WO 03/082167 | | 10/2003 |

OTHER PUBLICATIONS

Form PCT/ISA/210 (International Search Report) dated Jul. 13, 2006.

Form PCT/ISA/237 (Written Opinion of the international Searching Authority) dated Jul. 13, 2006.

English translation of the Decision of Rejection issued in corresponding Application No. JP 2008-547145 on Nov. 1, 2011.

* cited by examiner

REFASTENABLE PANT-LIKE ABSORBENT ARTICLE AND A METHOD FOR MAKING IT

TECHNICAL FIELD

The present disclosure refers to a pant-type refastenable absorbent article, such as a pant diaper, training pant, swim pant, sanitary pant or incontinence pant. The disclosure further refers to a method for making the refastenable absorbent article.

BACKGROUND

Pant-type absorbent articles have a defined waist opening and a pair of leg openings and are pulled onto the body of the wearer by inserting the legs into the leg openings and pulling the article up over the waist. They are usually provided with various elastic elements so that they can conform to the body of the user and provide a comfortable fit. Examples of such pant-type absorbent articles are pant diapers, sanitary pants and incontinence pants worn by incontinent adults. They comprise a first body panel and a second body panel, forming the front and back panels of the pant. The first and second body panels are joined to each other along lateral edges to form side connections. A crotch panel is provided between the first and second body panels. The crotch panel can be integral with either one or both panels or can be provided as a separate part joined to the first and second body panels.

Pant-type absorbent article often do not have a refastening mechanism that allows the garment to be easily removed after use or to be adjusted during use. However there are known through various prior art documents such refastenable pant-type absorbent articles.

WO 95/27462 discloses a pant diaper having releasable and refastenable fastening means along the lateral edges of the front and back panels for joining the front and back panels together along the sides thereof. The refastenable fastening means replaces a permanent side seam.

WO 01/87204 discloses an absorbent garment with a refastenable side seam. Complementary fasteners are applied at the front and the back panels on the wearer facing side and one of the complementary fasteners is applied to the panel in a C-folded configuration such that a lap seam is formed.

WO 03/024377 discloses a refastenable absorbent garment comprising a plurality of fastener pieces spaced along the side edges forming refastenable side seams of the garment. Cuts may be provided in the body panel webs between the fastener pieces.

WO 03/057116 discloses a refastenable absorbent garment having a fastening tab hingedly connected to the body facing side of a first body panel. The fastening tab is hinged and folded over along a folding line adjacent a lateral side edge of the body panel and is in the folded over state releasably fastened to the body facing side of the opposite body panel. No overlapping side seams between the first and second body panels are provided along their joined side edges.

One problem with these types of openable and refastenable absorbent garments is that it may be difficult to open the side seams in a controlled manner so that they may be refastened again. If the side seams are difficult to open, an attempt to open them may result in tearing of the web materials of the body panels, at which the garment will become unusable.

SUMMARY

The present disclosure aims at providing a pant-like absorbent articles such as a pant diaper, a training pant, a swim pant, a sanitary pant or incontinence pant, having openable and refastenable side connections. The side connections should be easy to open and re-connect in a controlled manner minimizing the risk for tearing of the web materials of the body panels.

According to an embodiment of the disclosure there is provided a pant-type absorbent article of the kind mentioned above, comprising a first body panel having a body facing side and a garment facing side and a second body panel having a body facing side and a garment facing side, the body facing sides of first and second body panels are joined to each other along or near at least one of their respective lateral edges by refastenable fastening means, comprising a first fastening member having a first portion attached to or near a lateral edge of the body facing side of the first body panel and having a second portion which is unattached to said first body panel, wherein the first fastening member comprises a hinge between said first and second portions, said hinge extending in a substantial longitudinal direction of the article. The portion of the first fastening member which is unattached to the first body panel is refastenably attached to a complementary second fastening member provided on the body facing side of the second body panel. The body facing sides of the first and second body panels are arranged in a face-to-face relationship along their lateral edges in the area of the first portion of the first fastening member.

According to one embodiment a recess is provided in the lateral edge of the first body panel. This recess forms a finger grip for facilitating opening of the side connections.

In one aspect of the disclosure at least part of said recess has an extension in a longitudinal direction of the article of at least 3 mm, preferably at least 5 and more preferably at least 10 mm.

In a further aspect the recess has an extension in a transverse direction of the article of at least 3 mm, preferably at least 5 mm.

According to one embodiment the recess extends through said first fastening member in the portion thereof which is attached to the first body panel.

According to a further embodiment the first and second fastening members are hook-and-loop type fasteners. In a preferred embodiment the first fastening member is a loop member and the second fastening member is a hook fastener.

In one aspect of the disclosure the second fastening member is applied on the second body panel at a distance of at least 3 mm, preferably at least 5 mm from the lateral side edge thereof.

In a further aspect the hinge of the first fastening member is located at a distance of at least 3 mm and preferably at least 5 mm from the lateral side edge of the first body panel.

According to one embodiment the length of the first fastening member as seen in longitudinal direction, y, is at least 75% of the length, a, of the side connections, preferably at least 90% of said length.

In a further embodiment the second fastening member is attached to the back body panel at a distance, b, of at least 3 mm, preferably at least 5 mm from the lateral side of the second body panel. In a still further embodiment the width in the transverse direction, x, of the second fastening member is at least 3 mm, preferably at least 5 mm, and the length in longitudinal direction, y, is substantially equal to the length of the first fastening member.

In a still further aspect at least part of the panel exposed in the recess and/or the surrounding edge of the recess is coloured in a contrasting colour or pattern.

The disclosure further refers to a method of making refastenable side connections in a pant-like absorbent article, said article having a longitudinal, y, and transverse direction, x, said method comprising the steps of:

- aligning a plurality of article blanks in a transverse direction, x, each article blank including first body panel and second body panel, wherein adjacent blanks are joined between their first body panels and between their second body panels at intended lines of separation, said article blanks having a body facing side and a garment facing side in its intended use as absorbent article;
- bonding a first fastening member of a refastenable fastening means to each of the first body panels, to the intended body facing side thereof, in such a way that one portion of the first fastening member is bonded to the first body panel, while a second portion thereof, is left unbonded, thus forming a hinged attachment of said first fastening member, comprising a hinge extending in a substantial longitudinal direction, y of the article;
- bonding a second fastening member of said refastenable fastening means to the second body panels, to the intended body facing side thereof;
- cutting a hole through the first body panel in the area of the intended line of separation between adjacent first body panels, so that said hole bridges adjacent first body panels;
- folding the article blanks to place the first fastening member of the first body panel of each blank in fastening contact with the second fastening member of the second body panel of the same blank;
- cutting the folded blanks along the intended line of separation to form pant-like absorbent articles therefrom;
- or alternatively cutting the blanks along the intended lines of separation before folding them.

In one embodiment said hole is cut also through the first fastening member bonded to the first body panel.

Definitions

Pant-Type Absorbent Article

Pant-type absorbent articles have a defined waist opening and a pair of leg openings and are pulled onto the body of the wearer by inserting the legs into the leg openings and pulling the article up over the waist. Examples of such pant-type absorbent articles are pant diapers, sanitary pants and incontinence pants worn by incontinent adults. Pant-type absorbent articles usually comprise a front body panel and a back body panel, which are joined to each other along two opposite longitudinal side edges to define a waist-opening and a pair of leg-openings. The pant-type absorbent article further comprises a crotch portion in the part of the article that in use is intended to extend through the wearer's crotch area, between the legs. The absorbent article is intended to be placed against the skin of the wearer to absorb and contain body exudates, like urine, faeces and menstrual fluid. The disclosure mainly refers to disposable absorbent articles, which means articles that are not intended to be laundered or otherwise restored or reused as absorbent articles after use.

Refastenable and Releasable Attachment

The term "refastenable" refers to a releasable attachment of two elements, thus the attachment may be separated and subsequently reattached without substantial permanent deformation or rupture. "Releasable attachment" refers to elements that are connected such that the elements tend to remain connected in the absence of a separation force being applied to one or both of the elements, and that the elements being capable of separation without substantial permanent deformation or rupture. The required separation force should typically be beyond that encountered while wearing the article.

Fixedly Attached

The term "fixedly attached" refers to two or more elements being attached to each other so that they are not intended to be separated or disconnected during normal use of the absorbent article.

Hook-and-Loop Fastener

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials Hook-and-loop fasteners are for example available from Velcro, USA.

Hinge

The term "hinge" refers to the folding line around which the second portion of the first fastening means which is unattached to the first body panel is allowed to flex.

Side Connection

The term "side connection" used in this context refers to the area along the lateral side edges of the first and second body panels where the body facing sides of said body panels are held in a face to face relationship by the refastenable fastening means. The actual fastening area between the refastenable fastening means does not necessarily have to be located in the area of the face to face oriented body facing sides of the body panels, but normally is located slightly inside thereof due to the hinged attachment of the first fastening means.

BRIEF DESCRIPTION OF THE FIGURES

The invention will in the following be more closely described with reference to an embodiment shown in the accompanying drawings.

DESCRIPTION OF PREFERRED EMBODIMENTS

Figure 1:
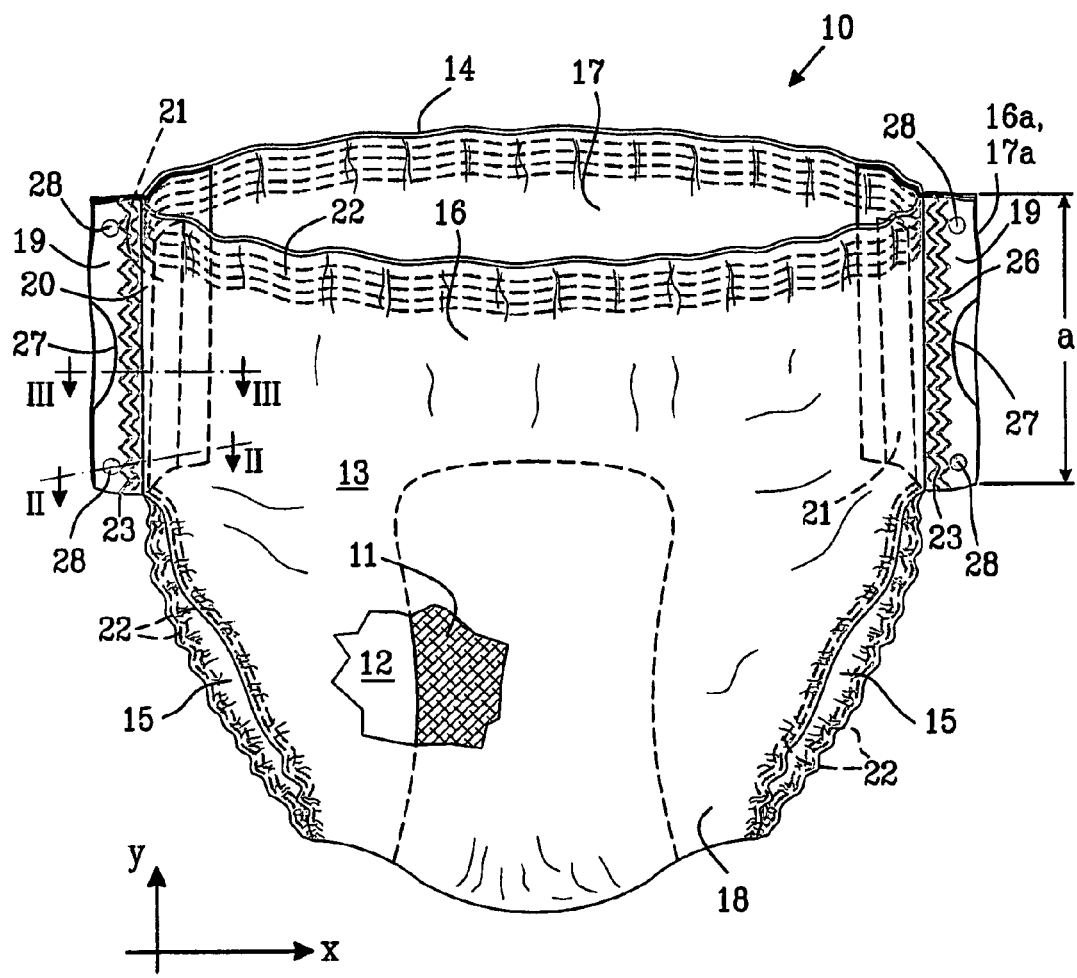
FIG. 1 shows a refastenable pant diaper.

The disclosure refers to pant-type absorbent articles 10, which have a defined waist opening 14 and a pair of leg openings 15 and which are pulled onto the body of the wearer by inserting the legs into the leg openings and pulling the article up over the waist. Examples of such pant-type absorbent article are pant diapers, training pants, swim pants, sanitary pants and incontinence pants worn by incontinent adults. The article will in the following be referred to as a "pant diaper". The article has a longitudinal direction x and a transverse direction y.

The pant diaper comprises a front body panel 16, which is the part of the pant diaper that in use is intended to extend over the stomach and front hip area of the wearer. The article also comprises a back body panel 17, which is the part of the article that in use is intended to extend over the back and the rear hip area of the wearer. The crotch portion 18 of a pant diaper article is the part of the diaper that in use is intended to extend through the wearer's crotch area, between the legs.

An absorbent core 11 is disposed in the crotch portion 18 and extends into the front and back body panels 16 and 17. The absorbent core is disposed between an inner coversheet 12 and an outer coversheet 13.

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wetlaid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

The "outer coversheet" refers to the material forming the outer cover of the absorbent article. The outer coversheet may be the same or different in different parts of the absorbent article. At least in the area of the absorbent core the outer coversheet comprises a liquid impervious material a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises a nonwoven material on at least the garment-facing surface thereof.

The "absorbent core" is the absorbent structure disposed between the two coversheets of the absorbent article in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

The front and back body panels 16 and 17 or those parts thereof that are located outside the absorbent core region may have different material composition than the crotch portion 18. Thus according to one embodiment the areas of the front and back body panels 16 and 17 which are located outside the absorbent core region may be composed of for example a laminate material having a body facing side and a garment facing side, while a liquid impervious outer coversheet and/or a liquid pervious inner coversheet only is present in the absorbent core region. In other embodiments the inner and outer coversheets are the same in the front and back body panels 16 and 17 as well as in the crotch region 18.

The lateral side edges of the front 16 and back body panels 17 are held together to form side connections 19, wherein the diaper assumes a pant-like shape having the aforementioned waist opening 14 and leg openings 15. The front and back portions are held together by refastenable fastening means, for example mechanical fastening means like hook-and-loop fasteners, or adhesive fasteners. The releasable fastening means comprises a first fastening member 20 and a second fastening member 21. The front and back body panels 16 and 17 are held together in a face to face relationship along their lateral edges 16a and 17a with their body facing sides facing inwards in the side connections 19.

The waist opening 14 and at least a part of the leg openings 15 are elasticized. The elastification is usually accomplished by a plurality of elastic members 22, such as elastic threads, which are contractably affixed between the outer coversheet 13 and the inner coversheet 12. Alternatively elastic materials, such as elastic laminates, may be used to form the front 16 and/or back body panels 17 in those areas where elasticity is desired.

The first fastening member 20 is fixedly attached to the body facing side of the front body panel 16. The attachment 23 may be accomplished by gluing, ultrasonic welding, thermobonding or the like. Only a first portion 24 of the first fastening member 20, as seen in the transverse direction, x, is attached to the front body panel 16, while a second portion 25 is unattached to the front body panel 16. This partial attachment of the first fastening member 20 is referred to as a hinged attachment since the second portion 25 is free to flex with respect to the front body panel 16. The folding line 26 around which the second portion 25 is allowed to flex is referred to as a hinge. The hinge 26 extends substantially in the longitudinal direction, y, of the article. The first fastening member 20 is preferably attached to the front body panel 16 along its entire longitudinal length. The first fastening member 20 is attached with its first portion 24 to the first body panel 16 adjacent or close to a lateral side edge 16a thereof while the second unattached portion 25 extends away from said lateral edge 16a.

The width of the first fastening member 20, as seen in the transverse direction, x, is at least mm, preferably at least 15 mm and more preferably at least 20 mm. It is preferred that this width is no more than 40 mm, preferably no more than 30 mm. The length of the first fastening member 20, as seen in longitudinal direction, y, is at least 75% of the length of the side connections 19, i.e. the distance, a, between the waist opening 14 and the respective leg opening 15, preferably at least 90% of said length. It would be possible to have two or more first fastening members 20 arranged at short intervals along the lateral edge 16a of the body panel 16, wherein said length corresponds to the distance between the outer edges of the outermost first fastening members 20.

The hinge 26 of the first fastening member 20 is located at least 3 mm, preferably at least 5 mm from the lateral side edge 16a of the first body panel 16. The width in transverse direction, x, of the second portion 25, which is unattached to the first body panel 16, is at least 5 mm, preferably at least 7 mm and more preferably at least 10 mm.

A recess 27 is provided in the lateral side edge 16a of the front body panel 16, said recess 27 extends also through the first fastening member 20. The recess has an extension of at least 5 mm, preferably at least 10 mm, in the longitudinal direction, y, and an extension in transverse direction, x, of at least 3 mm, preferably at least 5 mm.

The refastenable fastening means further comprises a second complementary fastening member 21, which is fixedly attached to the body facing side of the back body panel 17. The attachment may be accomplished by gluing, ultrasonic welding, thermobonding or the like. The second fastening member 21 is preferably attached to the back body panel 17 along its entire length and width.

In a preferred embodiment the first and second fastening members 20 and 21 are complementary hook-and-loop fasteners. It may in some cases be preferred that the first fastening member 20 is a loop member while the second fastening member 21 is a hook member, but the opposite is also feasible.

If the first fastening member 20 is a loop member and the second fastening member 21 is a hook member, it is preferred that the second fastening member has a length in longitudinal direction, y, which is substantially equal to or smaller than the length of the first fastening member 20. Its width in the transverse direction, x, is also smaller or equal to the width of the second portion 25 of the first fastening member 20. Thus in this case the second fastening member 21 is preferably smaller than or of equal size as the size of the portion of the first fastening member 20 to which it is attached. Also the second fastening member 21 may be composed of two or more fastening members arranged at short intervals along the lateral edge 17a of the body panel 17, wherein said length corresponds to the distance between the outer edges of the outermost second fastening members 21.

In an alternative embodiment the first fastening member 20 is a hook portion, wherein the body facing side of the respective body panel may form the second fastening member 21, the loop portion. In this case the second fastening member 21 can be larger than the first fastening member 20.

Figure 4:
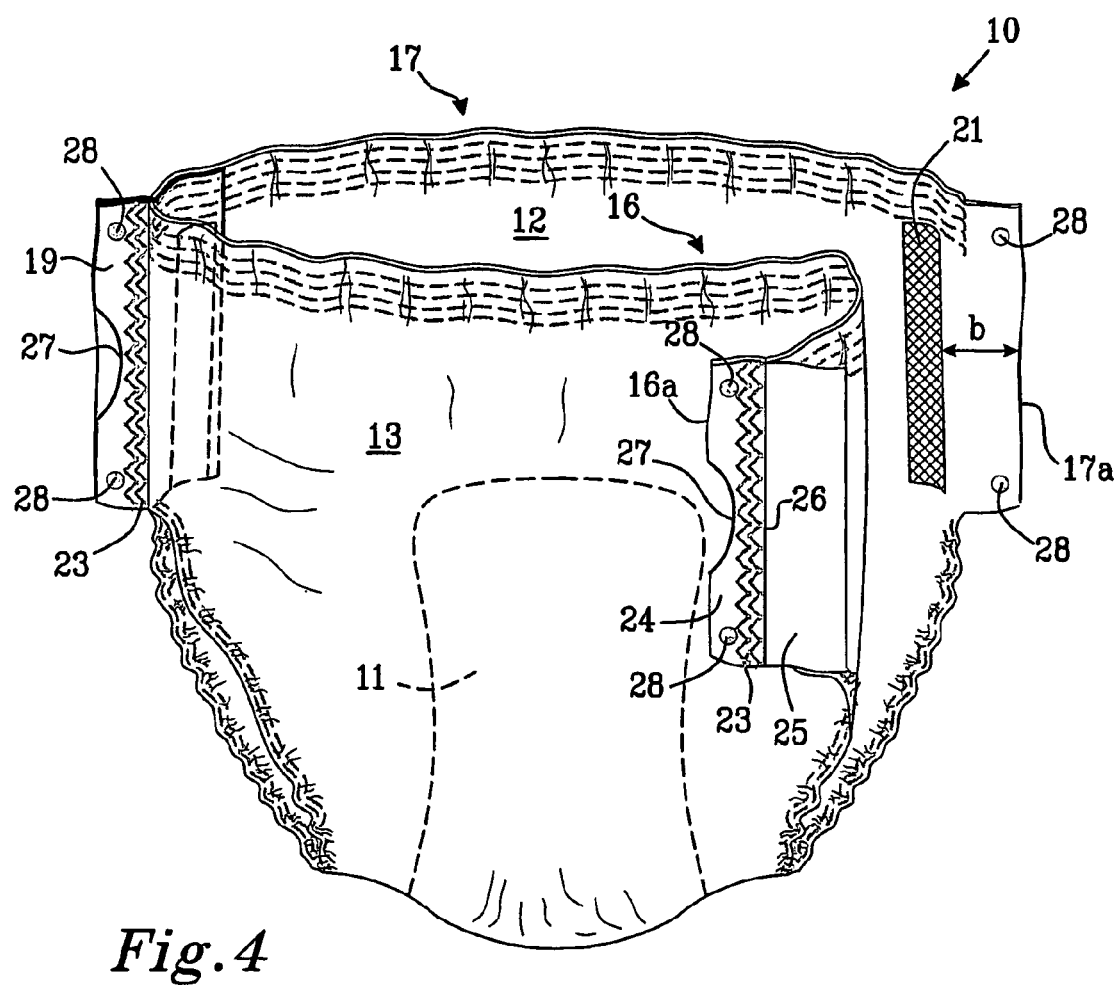
FIG. 4 shows the pant diaper according to FIG. 1 with one side connection opened.

The second fastening member 21 is attached to the back body panel 17 at a distance of at least 3 mm, preferably at least 5 mm from the lateral side 17a of the back body panel 17. This distance, b, is illustrated in FIG. 4. Preferably the distance b is equal to or longer than the distance between the hinge 26 of the first fastening member 20 and the lateral side edge 16a of the first body panel 16.

Figure 2:
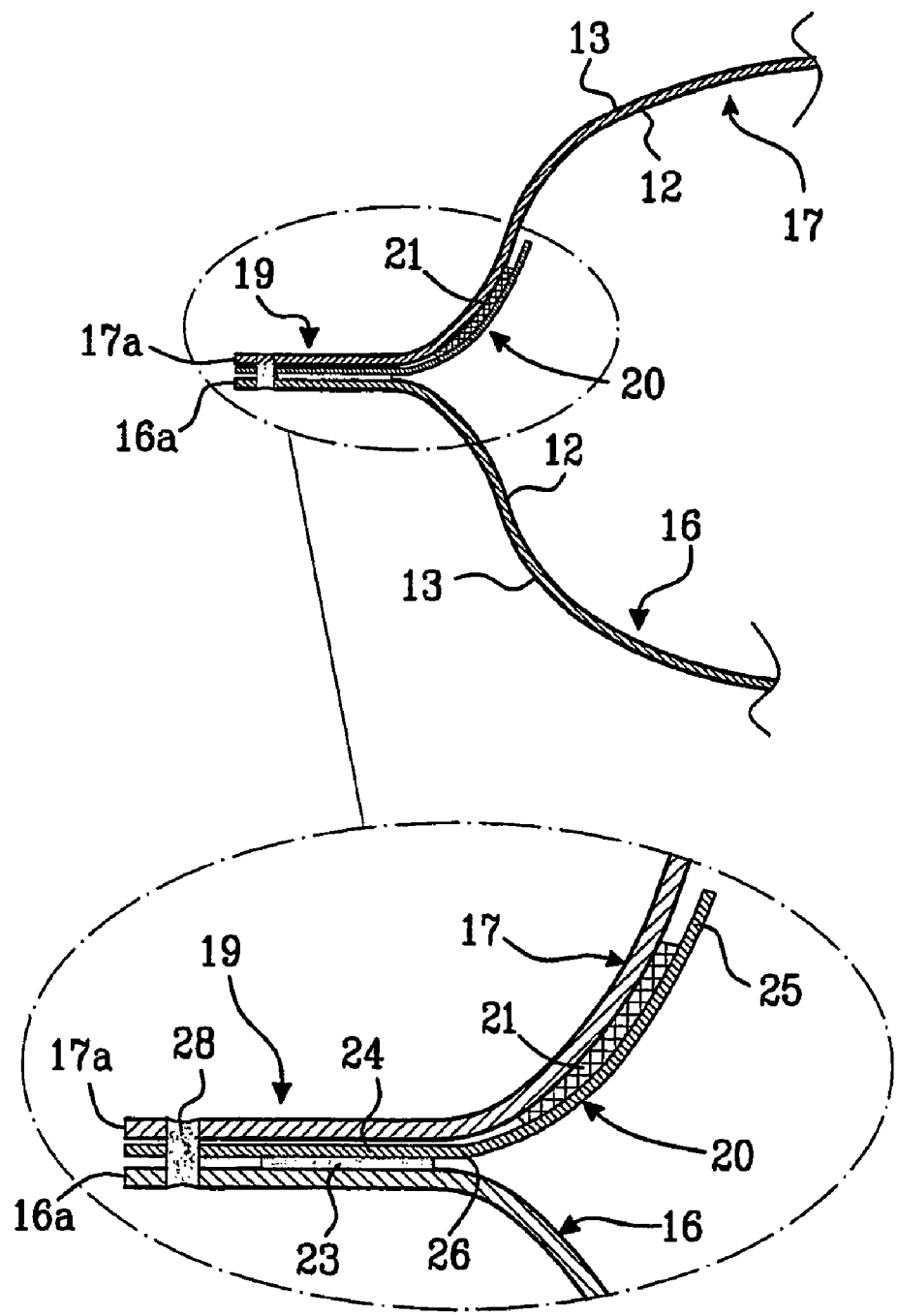
FIG. 2 is a cross-sectional view along the line II-II in FIG. 1.
Figure 3:
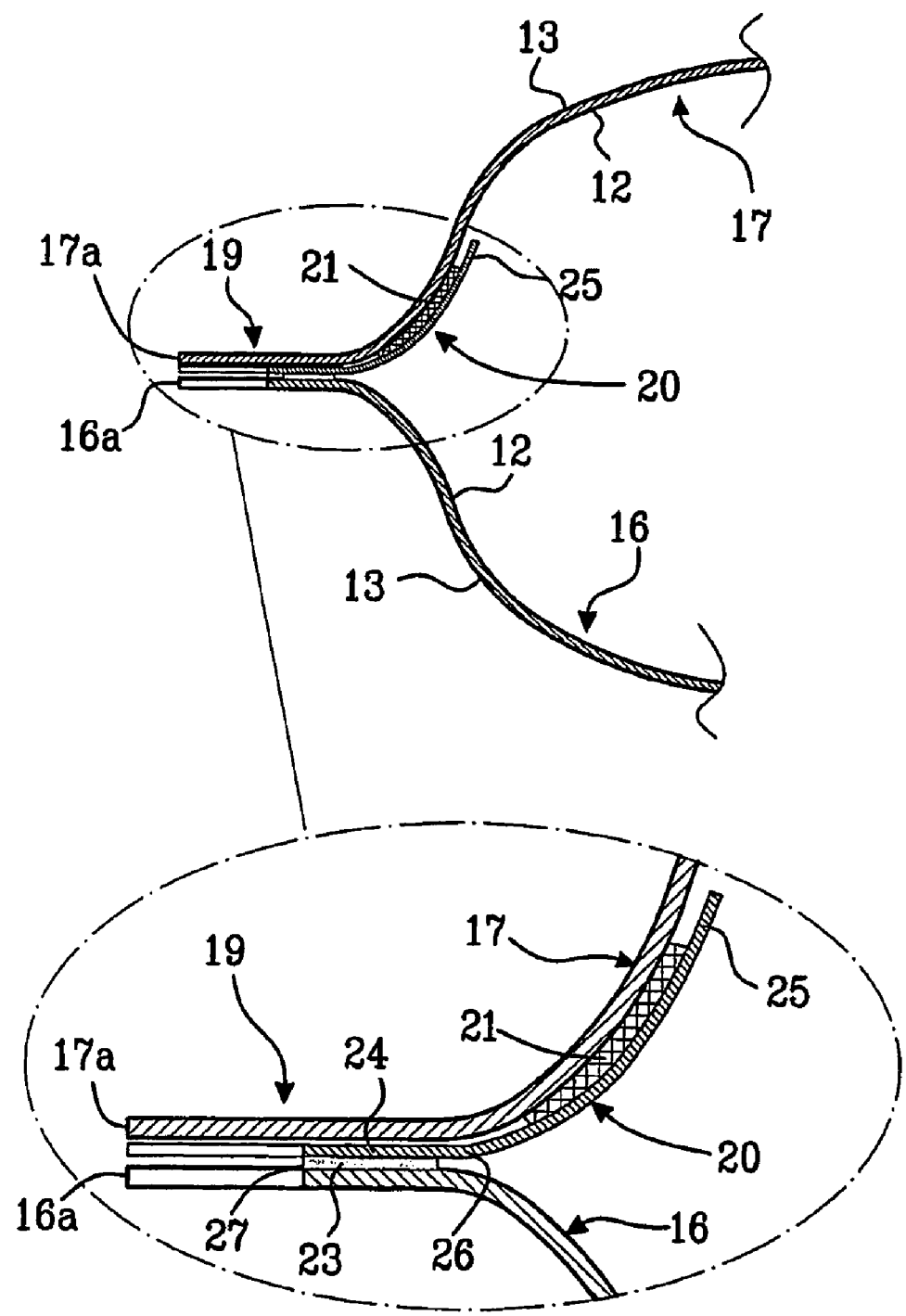
FIG. 3 is a cross-sectional view along the line III-III in FIG. 1.

The second portion 25 of the first fastening member 20 is in the closed position of the pant diaper releasably attached to the second fastening member 21 as best illustrated in FIG. 2. The first and second fastening members 20 and 21 hold the body facing sides of the front and back body panels 16 and 17 in a face to face relationship along their lateral edges 16a, 17a in the area of the first portion 24 of the first fastening member 20. Since the second portion 25 can flex about the hinge 26 it may easily move away from the front body panel 16.

It should be understood that any of the first and second fastening members 20 and 21 could form an integrated part of the body facing side of the respective body panel 16 or 17. Thus in the case of the first fastening member 21 being a hook portion the second fastening member may be a loop portion constituted by a nonwoven inner coversheet 12 of the respective body panel 16 or 17. It is also understood that the first fastening member 20 may be attached to the back body panel 17 and the second fastening member be attached to or form a part of the front body panel 16.

When opening the side connections 19, the recess 27 or rather the portion of the back panel 17 that is exposed in the recess 27, will act as a finger grip and a visual indication of where to initiate opening of the side connections 19, thus facilitating separation of the first and second fastening members 20 and 21. Thus the recess should preferably be large enough to accommodate a finger. It is evident that the recess 27 may be provided in the back panel 17 instead of in the front panel 16 as shown in the drawings.

In order to easily detect the location of the recess at least part of the recess 27 or rather the portion of the body panel that is exposed in the recess 27 and/or the surrounding edge of the recess 27 may be coloured in a contrasting colour.

In an alternative embodiment the recess 27 is eliminated and separation of the first and second fastening member 20 and 21 may be accomplished by pulling apart the lateral edges 16a and 17a of the body panels 16 and 17 in the side connection area 19.

The side connections 19 may be sealed by bonding sites 28, for example in the form of ultrasonic welding spots, glue spots, thermobonding spots. These bonding sites 28 should be small enough not to prevent opening of the side connections, and they may have any suitable shape and configuration. The bonding sites 28 will be destroyed when the side connections are opened for the first time.

While it has been described and shown above that the refastenable fastening means are provided along both lateral sides of the pant diaper, it should be understood that only one side of the pant diaper may be provided with refastenable fastening means, while the opposite side edges of the first and second body panels may be fixedly attached to each other, such as by gluing or ulatrasonic welding.

Referring to FIG. 5 a-e an embodiment of a process for making the above described refastenable pant diaper is illustrated. Although the process is described in terms of different steps, it should be understood that it is a continuous process.

A continuous web of material 29 comprising a plurality of absorbent article blanks aligned in a transverse direction (x), which will form the front, back and crotch panels of the pant diaper, is moved along a process line. The web 29 has longitudinal edges 29a and 29b A hole 30 has been made in the web 29 (aligned blanks), which will form the leg openings 14 of the pant diaper. Absorbent cores, elastic members etc. are also present with the blanks, but are not shown. A piece of material intended to form first fastening members 20 of two adjacent pant diapers is placed on the web 29 in the area between the hole 30 and one longitudinal edge 29a of the web 29, thus bridging the intended line of separation 31 between two adjacent pant diaper blanks. The fastening member 20 material is placed on the side of the blank that will form the body facing side, i.e. the inner coversheet. This piece of first fastening member material 20 is fixedly attached to the blank by gluing, ultrasonic welding, thermobonding or the like. In the embodiment shown, two stripes of attachment 23, spaced apart a selected distance, are provided, one for each pant diaper blank. Alternatively one single area of attachment 23 is bridging the intended line of separation between two adjacent pant diaper blanks.

In a further alternative two separate pieces of material intended to form first fastening members 20 of a pant diaper each are placed on either sides of the intended line of separation 31.

The stripe of attachment 23 does not extend the entire width of the respective first fastening member 20, but leaves a portion thereof, facing away from the intended line of separation between the adjacent pant diaper blanks, unattached to the blank. This will constitute the hinged attachment of the first fastening member 20 as described above. The area of attachment 23 may extend to the intended line of separation 31 of the adjacent pant diaper blanks or terminate a selected distance inside thereof.

A pair of second fastening members 21 are fixedly attached to each blank on either sides of the intended line of separation between the blanks, on the opposite side of the leg opening hole 31 as compared to the first fastening member 20. The second fastening members 21 are attached at a selected distance from said intended line of separation 31 forming the lateral side edge of the pant diaper, as discussed above. Alternatively a single piece of second fastening member 21 is attached to the adjacent pant diaper blanks, said piece of second fastening member bridging the intended line or separation 31.

A hole 32 is subsequently made through the combined first fastening member 20 and web 30. The hole 32 is centered with respect to the intended line of separation between the adjacent pant diaper blanks. The hole 32 will form the recesses 27 of both pant diapers to be formed from the blanks. Alternatively the hole 32 is made through only the web 30 before placing the first fastening member 20 thereon.

Figure 5A:
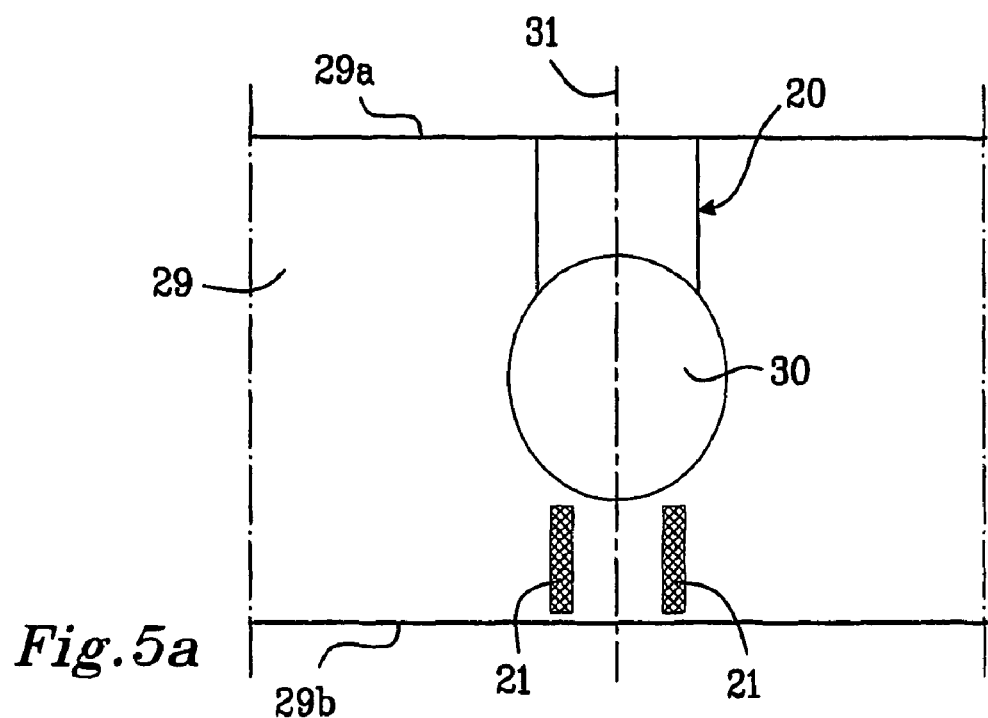
FIGS. 5 a-e illustrate schematically different manufacturing steps of one embodiment of making a refastenable pant diaper.
Figure 5B:
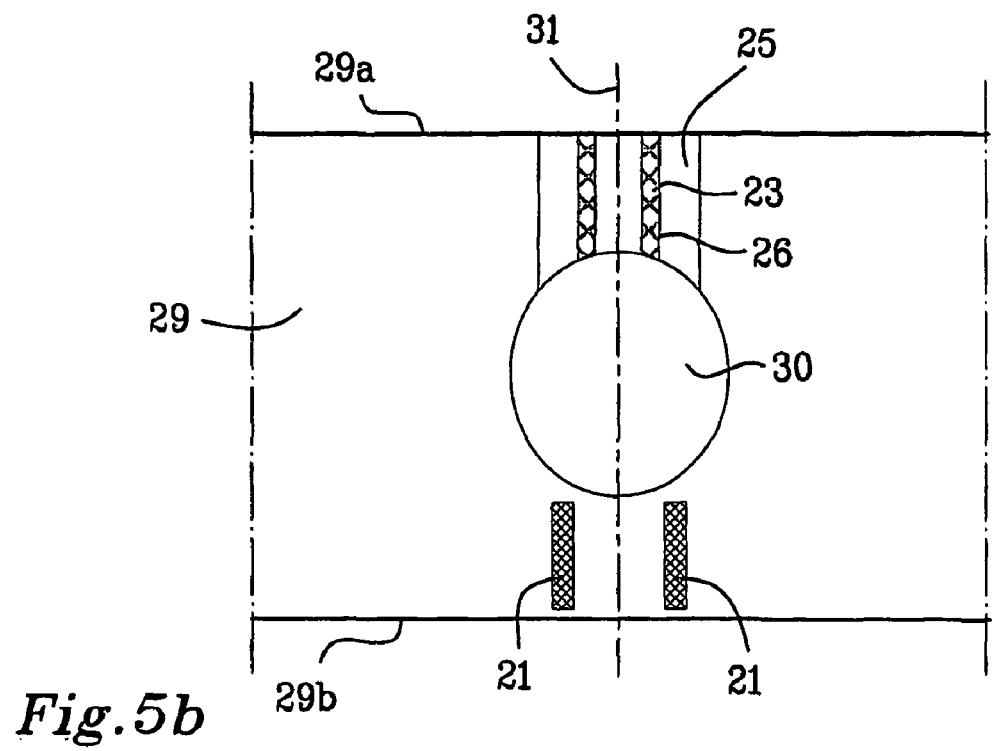
Figure 5C:
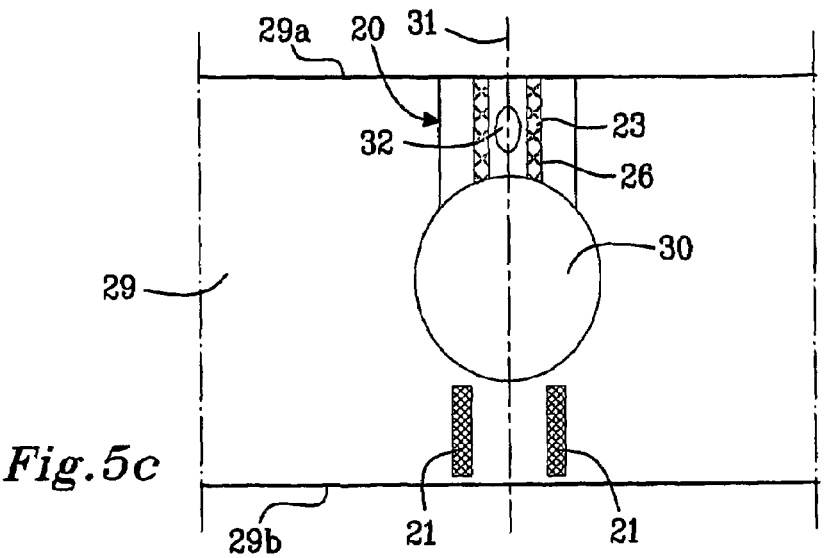
Figure 5D:
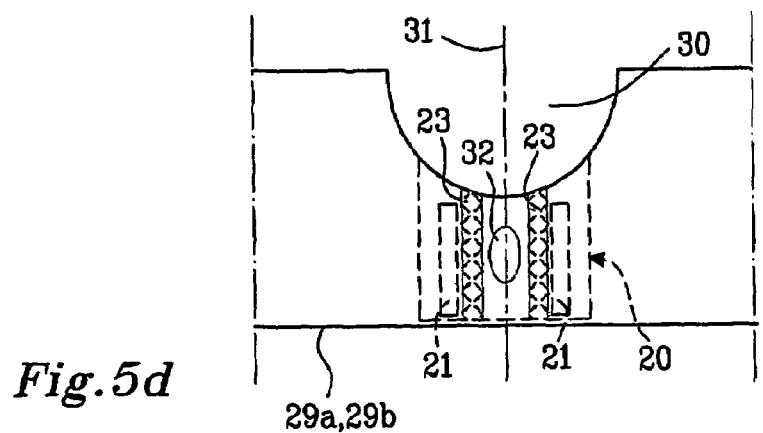
Figure 5E:
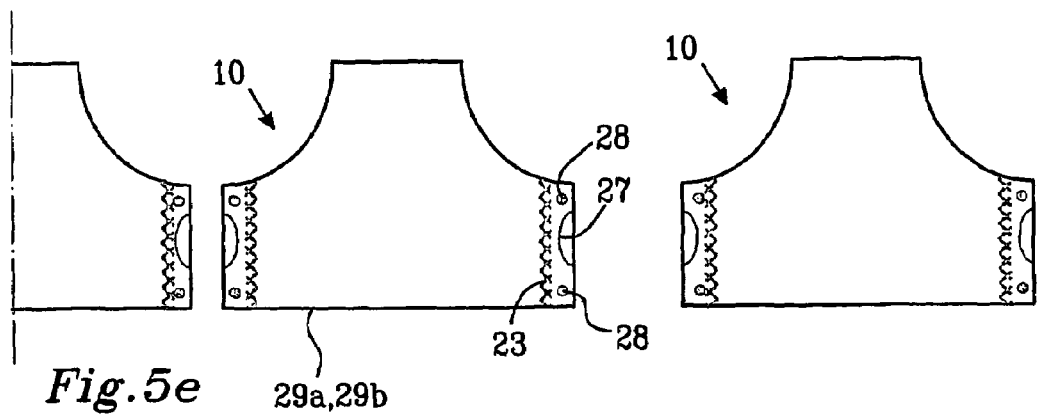

The blanks are then folded in the longitudinal direction as shown in FIG. 5d at which the first and second fastening members 20 and 21 will fasten to each other to form side connections. An additional sealing of the side connection area may be provided by bonding sites 28, for example ultrasonic welding spots, glue spots, thermobonding spots or the like. Cutting along the separation line 31 is then performed, as shown in FIG. 5e, to form the pant diapers. Alternatively cutting is performed before folding the blanks.

Additional process steps like adding a colouring or patterning agent to the area between the second fastening members 21, which will be exposed in the recess 27, or around the edges surrounding the recesses 27 (the hole 31) may be present, if desired.

The refastenable pant-type absorbent article according to an embodiment of the disclosure can also be manufactured in a longitudinal direction. A recess 32 in the form of a "half hole" can then be provided in each lateral edge of the first body panel.

While there have been shown and described and pointed out fundamental novel features of the invention as applied to preferred embodiments thereof, it will be understood that various omissions and substitutions and changes in the form and details of the devices, method steps and products illustrated may be made by those skilled in the art. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A refastenable pant-type absorbent article, said article having a longitudinal and a transverse direction and comprises a first body panel having a body facing side and a garment facing side and a second body panel having a body facing side and a garment facing side, said first and second body panels being joined to each other along or near at least one of their respective lateral edges by refastenable fastening means to form a side connection, said refastenable fastening means comprising a first fastening member having a first portion attached to or near a lateral edge of the body facing side of the first body panel and having a second portion which is unattached to said first body panel, wherein the first fastening member comprises a hinge between said first and second portions, said hinge extending in a substantial longitudinal direction of the article, said second unattached portion is refastenably attached to a complementary second fastening member provided on the body facing side of the second body panel, wherein the body facing sides of the first and second body panels are arranged in a face-to-face relationship along their lateral edges in the area of the first portion of the first fastening member, wherein a recess is provided in the form of a cut-out in the lateral edge of the first body panel, wherein said recess extends through said first fastening member in the first portion thereof which is attached to the first body panel.

2. The absorbent article according to claim 1, wherein at least part of said recess has an extension in a longitudinal direction of the article of at least 3 mm.

3. The absorbent article according to claim 1, wherein said recess has an extension in a transverse direction of the article of at least 3 mm.

4. The absorbent article according to claim 1, wherein the first and second fastening members are hook-and-loop type fasteners.

5. The absorbent article according to claim 4, wherein the first fastening member is a loop member and the second fastening member is a hook fastener.

6. The absorbent article according to claim 1, wherein the second fastening member is located on the second body panel at a distance of at least 3 mm from the lateral side edge thereof.

7. The absorbent article according to claim 1, wherein the hinge of the first fastening member is located at a distance of at least 3 mm from the lateral side edge of the first body panel.

8. The absorbent article as claimed in claim 1, wherein the width in transverse direction of the second portion of the first fastening member, which is unattached to the first body panel, is at least 5 mm.

9. The absorbent article as claimed in claim 1, wherein the length of the first fastening member as seen in longitudinal direction is at least 75% of the length of the side connection.

10. The absorbent article as claimed in claim 1, wherein the first body panel is a front body panel adapted to extend over the stomach and front hip area of a user, and the second body panel is a back panel adapted to extend over the back and rear hip area of the user,
wherein the second fastening member is attached to the back body panel at a distance of at least 3 mm from the lateral side of the back body panel.

11. The absorbent article as claimed in claim 1, wherein the width in the transverse direction of the second fastening member is at least 3 mm, and the length in longitudinal direction is substantially equal to the length of the first fastening member.

12. The absorbent article according to claim 1, wherein at least part of the portion exposed in the recess and/or the surrounding edge thereof is coloured in a contrasting colour or patterned.

13. The absorbent article according to claim 1, wherein at least part of said recess has an extension in a longitudinal direction of the article of at least 10 mm and wherein said recess has an extension in a transverse direction of the article of at least 5 mm.

14. The absorbent article according to claim 10, wherein the first fastening member is a loop member and the second fastening member is a hook fastener.

15. The absorbent article according to claim 1, wherein first fastening member is fixedly attached to the first body panel and wherein second fastening member is fixedly attached to the second body panel.

16. The absorbent article according to claim 1, wherein the first fastening member comprises two or more part first fastening members arranged at short intervals along the lateral edge of the first body panel.

17. The absorbent article according to claim 5, wherein the second fastening member is integrated part of the second body panel.

18. The absorbent article according to claim 1, wherein the front and second body panels are joined to each other along or near at least one of their respective lateral edges by at least one non-refastenable bonding point.

19. The absorbent article according to claim 18, wherein the bonding points are at least one of ultrasonic welding spots, glue spots and thermobonding spots.

20. A refastenable pant-type absorbent article, said article having a longitudinal and a transverse direction and comprises a first body panel having a body facing side and a garment facing side and a second body panel having a body facing side and a garment facing side, said first and second body panels being joined to each other along or near at least one of their respective lateral edges by refastenable fastening means to form a side connection, said refastenable fastening means comprising a first fastening member having a first portion attached to or near a lateral edge of the body facing side of the first body panel and having a second portion which is unattached to said first body panel, wherein the first fastening member comprises a hinge between said first and second portions, said hinge extending in a substantial longitudinal direction of the article, said second unattached portion is refastenably attached to a complementary second fastening member provided on the body facing side of the second body panel,
wherein the body facing sides of the first and second body panels are arranged in a face-to-face relationship along their lateral edges in the area of the first portion of the first fastening member,
wherein the front and second body panels are joined to each other along or near at least one of their respective lateral edges by at least one non-refastenable bonding point, the at least one bonding point being located closer to the respective lateral edge than where the first portion of the first fastening member is attached to the first body panel.

21. The absorbent article according to claim 20, wherein the bonding points are at least one of ultrasonic welding spots, glue spots and thermobonding spots.

* * * * *